United States Patent
Lee et al.

(10) Patent No.: US 11,484,246 B2
(45) Date of Patent: Nov. 1, 2022

(54) APPARATUS AND METHOD FOR PROCESSING SPECTRUM ACCORDING TO CHANGE IN TEMPERATURE OF OBJECT

(71) Applicant: SAMSUNG ELECTRONICS CO., LTD., Suwon-si (KR)

(72) Inventors: Jun Ho Lee, Incheon (KR); Sang Kyu Kim, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 825 days.

(21) Appl. No.: 16/426,697

(22) Filed: May 30, 2019

(65) Prior Publication Data
US 2020/0121244 A1    Apr. 23, 2020

(30) Foreign Application Priority Data
Oct. 17, 2018   (KR) .................. 10-2018-0123961

(51) Int. Cl.
*A61B 5/00*    (2006.01)
*G01J 3/433*    (2006.01)
(Continued)

(52) U.S. Cl.
CPC .......... *A61B 5/443* (2013.01); *A61B 5/0002* (2013.01); *A61B 5/0075* (2013.01);
(Continued)

(58) Field of Classification Search
CPC ... A61B 5/1491; A61B 5/1455; A61B 5/0059; A61B 5/14532; A61B 5/01;
(Continued)

(56) References Cited

U.S. PATENT DOCUMENTS 5,740,079 A      4/1998  Shigemori et al.
6,161,028 A  *  12/2000  Braig .................. A61B 5/0059
                                                                   250/341.6
(Continued)

FOREIGN PATENT DOCUMENTS

JP              4247742 B2     4/2009
KR         10-0288310 b1     5/2001
(Continued)

OTHER PUBLICATIONS

Wu et al., "Near-Infrared Diffuse Reflectance Measurement Method Based on Temperature Insensitive Radial Distance", Jun. 18, 2018, Applied Spectroscopy, 72(7), 1021-1028. 17 pages total.
(Continued)

*Primary Examiner* — Puya Agahi
(74) *Attorney, Agent, or Firm* — Sughrue Mion, PLLC (57) ABSTRACT

Provided is a spectrum processing apparatus for removing noise, caused by a change in temperature, from a spectrum. The spectrum processing apparatus includes: a temperature modulator configured to perform modulation of a temperature of an object; a spectrometer configured to obtain a first spectrum based on the temperature of the object that is changed by the modulation; and a spectrum processor configured to extract a temperature change vector based on the first spectrum, and to correct a second spectrum based on the extracted temperature change vector.

17 Claims, 9 Drawing Sheets

(51) Int. Cl.
*G01J 3/02* (2006.01)
*A61B 5/1455* (2006.01)
*G01J 3/42* (2006.01)
*A61B 5/1491* (2006.01)

(52) U.S. Cl.
CPC .......... *A61B 5/1455* (2013.01); *A61B 5/7203* (2013.01); *G01J 3/0286* (2013.01); *G01J 3/433* (2013.01); *A61B 5/0059* (2013.01); *A61B 5/1491* (2013.01); *A61B 2560/0223* (2013.01); *A61B 2562/0271* (2013.01); *G01J 3/42* (2013.01)

(58) Field of Classification Search
CPC .. A61B 5/7203; A61B 2562/0271; G01J 3/42; G01J 3/0286; G01J 3/433
See application file for complete search history.

(56) References Cited

U.S. PATENT DOCUMENTS

| | | | |
|---|---|---|---|
| 6,198,949 B1 * | 3/2001 | Braig | G01J 3/0291 250/341.6 |
| 6,633,771 B1 * | 10/2003 | Braig | A61B 5/14532 250/341.6 |
| 8,172,459 B2 | 5/2012 | Abreu | |
| 8,734,536 B2 | 5/2014 | Beck et al. | |
| 8,941,382 B2 | 1/2015 | Hiller et al. | |
| 9,119,530 B2 | 9/2015 | Abreu | |
| 9,445,767 B2 | 9/2016 | Abreu | |
| 2007/0106172 A1 | 5/2007 | Abreu | |
| 2010/0081622 A1 | 4/2010 | Hartmann et al. | |
| 2012/0316459 A1 | 12/2012 | Abreu | |
| 2017/0095205 A1 | 4/2017 | Abreu | |
| 2018/0020956 A1 | 1/2018 | Lee | |

FOREIGN PATENT DOCUMENTS

| | | |
|---|---|---|
| KR | 10-2008-0071145 a | 8/2008 |
| KR | 10-1750800 B1 | 6/2017 |
| KR | 10-2018-0011646 A | 2/2018 |

OTHER PUBLICATIONS

Hazen, "Temperature-Insensitive Near-Infrared Spectroscopic Measurement of Glucose in Aqueous Solutions", Applied Spectroscopy, vol. 48, No. 4, Nov. 1994, pp. 477-483, 7 pages total.

* cited by examiner

APPARATUS AND METHOD FOR PROCESSING SPECTRUM ACCORDING TO CHANGE IN TEMPERATURE OF OBJECT

CROSS-REFERENCE TO RELATED APPLICATION(S)

This application claims priority from Korean Patent Application No. 10-2018-0123961, filed on Oct. 17, 2018, in the Korean Intellectual Property Office, the entire disclosure of which is incorporated herein by reference for all purposes.

BACKGROUND

1. Field

Apparatuses and methods consistent with example embodiments relate to apparatuses and methods for processing spectrum according to a change in temperature of an object, and more particularly, to technology for removing noise, caused by the change in temperature of an object, from a spectrum measured from the object.

2. Description of the Related Art

Recently, research has been conducted on methods of measuring bio-information, such as blood glucose, in a non-invasive manner such as using Raman spectroscopy or near-infrared spectroscopy. A bio-information measuring apparatus using spectroscopy generally includes a light source which emits light onto an object, and a detector which detects an optical signal returning from the object. The bio-information measuring apparatus reconstructs a spectrum by using the optical signal detected by the detector, and measures in vivo components, such as blood glucose, calories, and the like, by analyzing the reconstructed spectrum. Generally, a scattered spectrum is affected by a change in temperature. In the case of a large spectrometer, the effect of temperature may be insignificant because the large spectrometer has a temperature control system to control the temperature of a system itself. However, it is difficult to provide such temperature control system for a small size spectrometer.

SUMMARY

According to an aspect of an example embodiment, there is provided a spectrum processing apparatus including: a temperature modulator configured to perform modulation of temperature of an object; a spectrometer configured to obtain a first spectrum based on the temperature of the object which is changed by the modulation; and a spectrum processor configured to extract a temperature change vector, which represents characteristics of respective wavelengths according to a change in temperature, based on the first spectrum, and to correct a second spectrum based on the extracted temperature change vector.

The temperature modulator may include: a heater configured to supply heat energy to the object; and a temperature sensor configured to detect the temperature.

The temperature modulator may perform the modulation to change the temperature of the object by 1° C. or more.

The temperature modulator may perform the modulation of the temperature of the object one or more number of times to change the temperature of the object within a predetermined range of temperature.

The temperature modulator may successively perform first modulation and second modulation, such that the temperature of the object is continuously increased by the first modulation and the second modulation within the predetermined range of temperature.

The temperature modulator may perform first modulation of the temperature, and perform second modulation in response to the temperature of the object being decreased to temperature at a time of starting the first modulation, such that the temperature of the object is changed by the first modulation within the same range as a changed temperature of the object by the second modulation.

The spectrometer may obtain the first spectrum by using at least one of Infrared spectroscopy and Raman spectroscopy.

The spectrometer may include: one or more light sources configured to emit light onto the object; and a detector configured to detect light scattered and/or reflected from the object.

The spectrum processor may extract the temperature change vector based on at least one of Principal Component Analysis (PCA) and Singular Value Decomposition (SVD).

The spectrum processor may remove noise, caused by the change in temperature, from the second spectrum by applying a noise removal method including a least square method based on the extracted temperature change vector.

The spectrometer may obtain the first spectrum from the object that comprises at least one of a pure water solution and human skin containing a target component, and obtain the second spectrum from a second object comprising the human skin containing the target component.

The spectrum processing apparatus may further include an output interface configured to output a processing result of the spectrum processor.

The spectrum processing apparatus may further include a communication interface configured to transmit a processing result of the spectrum processor to an external device.

According to an aspect of another example embodiment, there is provided a spectrum processing method including: performing modulation of temperature of an object; obtaining a first spectrum based on the temperature of the object which is changed by the modulation; extracting a temperature change vector, which represents characteristics of respective wavelengths according to a change in temperature, based on the first spectrum; and correcting a second spectrum based on the extracted temperature change vector.

The performing of the modulation may include performing modulation to change the temperature of the object by 1° C.

The performing of the modulation may include performing modulation one or more number of times to change the temperature of the object within a predetermined range of temperature.

The extracting of the temperature change vector may include extracting the temperature change vector based on at least one of Principal Component Analysis (PCA) and Singular Value Decomposition (SVD).

The correcting of the second spectrum may include removing noise, caused by the change in temperature, from the second spectrum by applying a noise removal method including a least square method based on the extracted temperature change vector.

The obtaining the first spectrum may include obtaining the first spectrum from the object that includes at least one of a pure water solution and human skin containing a target component; and obtaining the second spectrum from a second object including the human skin containing the target component.

The spectrum processing method may further include outputting the corrected second spectrum.

BRIEF DESCRIPTION OF THE DRAWINGS

The above and/or other aspects will be more apparent by describing certain example embodiments with reference to the accompanying drawings, in which.

DETAILED DESCRIPTION

Details of example embodiments are included in the following detailed description and drawings. Aspects of example embodiments will be more clearly understood from the following embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part'. 'unit' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of a spectrum processing apparatus and a spectrum processing method will be described in detail with reference to the accompanying drawings.

Various embodiments of the spectrum processing apparatus which will be described below may be embedded in various information processing devices such as a mobile wearable device, a smart device, and the like. Examples of the various information processing devices may include, but are not limited to, a wearable device of various types such as a smart watch worn on the wrist, a smart band-type wearable device, a headphone-type wearable device, a hairband-type wearable device, and the like, a mobile device such as a smartphone, a tablet PC, and the like, or a specialized medical institution system, and the like.

Figure 1:
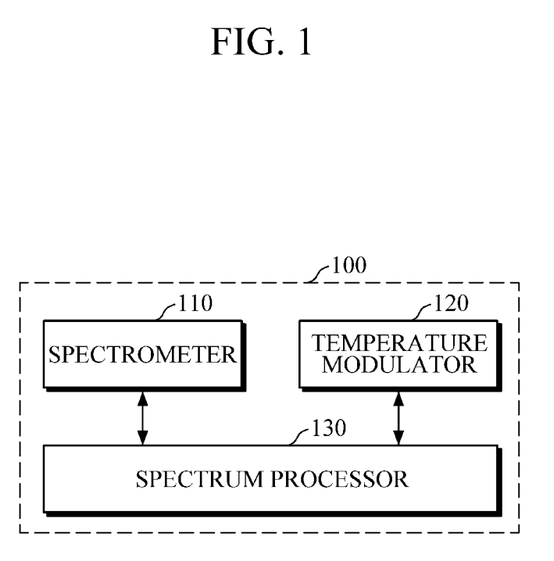
FIG. 1 is a block diagram illustrating a spectrum processing apparatus according to an example embodiment.

FIG. 1 is a block diagram illustrating a spectrum processing apparatus according to an example embodiment.

Referring to FIG. 1, the spectrum processing apparatus 100 includes a spectrometer 110, a temperature modulator 120, and a spectrum processor 130.

The spectrometer 110 may measure a spectrum from an object. The spectrometer 110 may measure a spectrum using Raman spectroscopy or near-infrared spectroscopy. In this case, the object may be an object used as a reference for calibration, and may be a pure water solution containing no target component to be analyzed, e.g., glucose, or a body tissue in an empty-stomach state. Alternatively, the object may be a body tissue containing a target component to be analyzed, and may be a human skin tissue, e.g., a portion of the radial artery, a top portion of the wrist where veins or capillaries pass, fingers, and the like.

The spectrometer 110 may include a light source which emits light onto an object, and a detector which detects light scattered or reflected from the object. The light source may include a light emitting diode (LED), a laser diode, a fluorescent body, and the like. The detector may include one pixel or a pixel array including two or more pixels, in which each pixel may include a photo diode or a photo transistor. Upon detecting light, the detector may convert the detected light signal into an electric signal. A light concentrator, such as a microlens, for improving light collection efficiency, may be disposed on the top of each pixel.

For example, the spectrometer 110 may include an array of a plurality of light sources, each of which emits light of different wavelengths. In this case, a color filter may be disposed on the top of at least some of the light sources to transmit or block light in a specific wavelength region. However, the spectrometer 110 is not limited thereto, and may be a spectrometer which measures a spectrum using various spectroscopic methods such as Raman spectroscopy, near-infrared spectroscopy, and the like.

The temperature modulator 120 may modulate temperature of an object while the spectrometer 110 measures a spectrum from the object. The temperature modulator 120 may perform modulation according to a predetermined modulation condition. In this case, the modulation condition may include a range of temperature to be modulated for each user, a number of times to perform modulation of temperature, a degree of change in temperature during modulation of temperature, and the like.

For example, when the temperature modulator 120 changes temperature of an object within a predetermined range, a spectrum measured by the spectrometer 110 may include noise caused by the temperature change of the object. The temperature modulator 120 may perform modulation of temperature one or more number of times during measurement of the spectrum. For example, in the case where the temperature modulator 120 performs modulation a plurality of times, the temperature modulator 120 may perform second modulation successively after first modulation ends, so that every time the temperature modulator 120 performs modulation, the temperature of an object may be continuously increased within a predetermined range of temperature. Alternatively, in the case where the temperature modulator 120 performs modulation a plurality of times, the temperature modulator 120 may perform second modulation after the first modulation ends and the temperature of an object is decreased to a temperature at the time of starting the first modulation, so that every time the temperature modulator 120 performs modulation, the temperature of an object may be changed within the same range.

Further, the temperature modulator 120 may perform modulation of temperature to change temperature by 1° C. or more every time the temperature modulator 120 performs temperature modulation. Generally, a spectrum obtained from an object may include noise caused by a change in temperature, humidity, and the like of the object due to factors derived from an external environment and/or the object itself. In an example embodiment, in order to effectively remove noise, caused by a change in temperature, from the measured spectrum, temperature modulation of the object is performed so that the temperature of the object is changed by 1° C. or more, thereby minimizing an effect derived from other factors.

The temperature modulator 120 may include a heater (not shown) and a temperature sensor (not shown). The heater may supply heat energy to an object for temperature modulation of the object. The temperature sensor may measure temperature of the object which is changed by the heat energy supplied by the heater. By interaction of the heater with the temperature sensor, modulation of temperature of the object may be performed.

For example, when the heater starts to supply heat energy to an object under the control of the spectrum processor 130, the temperature sensor may measure in real time the temperature of the object. Further, the temperature sensor may provide feedback on the measured temperature information to the heater. Based on the temperature information received from the temperature sensor, the heater may determine whether the temperature of the object reaches a target temperature. In the case where the temperature of the object does not reach the target temperature, the heater may further supply heat energy to the object.

In the embodiment, it is assumed that the spectrometer 110 and the temperature modulator 120 are integrally formed in a single hardware device, but the configuration is not limited thereto.

The spectrum processor 130 may be electrically connected to the spectrometer 110 and the temperature modulator 120. In response to a request for measuring a spectrum, the spectrum processor 130 may control the spectrometer 110 and the temperature modulator 120.

The spectrum processor 130 may receive an electric signal related to a spectrum for each change in temperature, which is measured during modulation of temperature of an object, and may process the received electric signal.

For example, in the case where the spectrometer 110 includes an array of a plurality of light sources which emit light of different wavelengths, the spectrum processor 130 may reconstruct a spectrum of an object by using the electric signal received from the spectrometer 110. The reconstructed spectrum may be used to analyze components of an object. The components of the object may include blood glucose, calories, alcohol, triglycerides, proteins, cholesterol, uric acid, and the like.

Further, in order to effectively analyze the components of the object by using the reconstructed spectrum, the spectrum processor 130 may remove noise, caused by a change in temperature, from the reconstructed spectrum. To this end, the spectrum processor 130 may extract a temperature change vector, which represents characteristics for respective wavelengths of the spectrum, based on a spectrum according to a change in temperature of an object. For example, the spectrum processor 130 may extract the temperature change vector by using Principal Component Analysis (PCA), Singular Value Decomposition (SVD), and the like, but is not limited thereto.

In addition, upon extracting the temperature change vector, the spectrum processor 130 may correct a spectrum by using the extracted temperature change vector. In this case, the spectrum processor 130 may remove noise of a spectrum by using a noise removal method such as a least square method and the like.

For example, once a spectrum is measured from an object for calibration, the spectrum processor 130 may extract the temperature change vector based on the measured spectrum and may store the extracted temperature change vector. Further, once a spectrum is measured from an object to measure a target component, the spectrum processor 130 may remove noise, caused by a temperature change, from the measured spectrum by using the temperature change vector.

Figure 2:
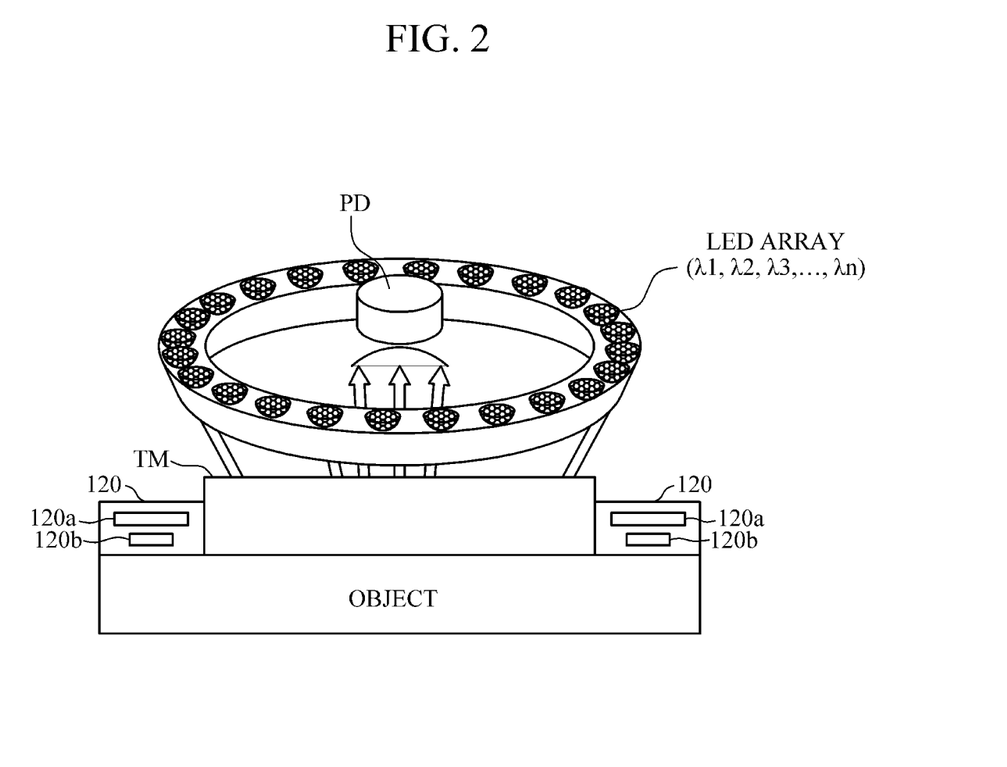
FIG. 2 is a diagram schematically illustrating a structure of a spectrum processing apparatus according to an example embodiment.

FIG. 2 is a diagram schematically illustrating a structure of a spectrum processing apparatus according to an example embodiment.

Referring to FIGS. 1 and 2, the spectrometer 110 of the spectrum processing apparatus 100 includes an LED array having N number of LED light sources arranged on a circular frame. Further, a photodiode detector PD may be disposed at the center of the circular frame. Here, a shape of the frame is not limited to a circular shape, and may be modified depending on devices in which the spectrum processing apparatus 100 is mounted.

Each LED light source may have at least some of peak wavelengths $\lambda_1, \lambda_2, \lambda_3, \ldots$, and $\lambda_n$ in different wavelength bands. The peak wavelengths of each LED may be preset, and may be set based on a spectrum measurement portion, a target component to be analyzed, and the like.

Each LED may sequentially emit the wavelengths $\lambda_1, \lambda_2, \lambda_3, \ldots$, and $\lambda_n$ onto the object in a time-division manner. In this case, driving conditions of light sources, which include a driving sequence, a driving time, and the like of light sources, may be preset. After light is emitted by each of the LEDs onto the object for component analysis, the emitted light is absorbed into, or reflected or scattered from the object depending on tissue properties of the object. In this case, photoreaction properties of the object may vary depending on the types of the object and the wavelengths of light, and the degree of absorption, reflection, transmission, or scattering of light by the object may vary depending on the photoreaction properties of the object.

One or more temperature modulators 120 may be disposed near a hole, through which light emitted by the LED array and light scattered or reflected from an object passes, or near a transparent material TM. As described in FIG. 2, the temperature modulator 120 includes a heater 120a for supplying heat energy to an object, and a temperature sensor 120b for measuring temperature of the object. The heater 120a and the temperature sensor 120b may interact with each other to allow for modulation of temperature.

The spectrum processor 130 may be electrically connected to the spectrometer 110 and the temperature modulator 120. In order to obtain a spectrum, the spectrum processor 130 may control the temperature modulator 120 to perform modulation of temperature of the object. A condition for temperature modulation may be predetermined. For example, a range of temperature for modulation and the like may be predetermined according to a measurement portion of a user, an external environment (e.g., external temperature at normal times, etc.) of an area where the user lives, and the like.

At the same time when controlling modulation of temperature, the spectrum processor 130 may drive each LED of the LED array. The spectrum processor 130 may sequentially drive each LED of the LED array. However, the driving of the LED array is not limited thereto and driving conditions of each LED, which include a driving sequence, a driving time, and the like of each LED, may be preset according to various measurement circumstances, e.g., a shape of a mounted device, a measurement portion, and a target component to be analyzed, and the like.

The spectrum processor 130 may receive a signal according to a response of the object from the detector PD of the spectrometer 110. The spectrum processor 130 may reconstruct a spectrum based on the signal received from the detector PD.

For example, the spectrum processor 130 may obtain a linearly independent equation based on a data set of signals according to a response of the object detected by the detector PD, and may reconstruct a spectrum based on the linearly independent equation. For example, the spectrum processor 130 may obtain a linear equation written in matrix form as represented by the following Equation 1, and may obtain the reconstructed spectrum by using a method of solving the linear equation.

$$Az = U \quad \text{[Equation 1]}$$

Herein, A is a matrix of properties of a reference spectrum measured according to driving conditions of each light source; U is a matrix of values actually measured from the object for component analysis under the same driving conditions of each light source; and z is a spectrum to be recovered. In this case, there may be an ill-conditioned matrix A, in which a system value of Equation 1, which is a linear equation, may be incorrect. In such a case, by using a solution to an inverse problem, a spectrum of an object may be recovered with no limitations on the resolution size of the spectrum, and with high accuracy by using a minimum number of spectrum curves that are used. The inverse problem may be solved by Tikhonov regularization method, which is represented by the following Equation 2.

$$(\alpha E + A^T A) Z_\alpha = A^T u$$

$$Z_\alpha = (\alpha E + A^T A)^{-1} A^T u \quad \text{[Equation 2]}$$

Herein, u is each component of a matrix U actually measured by the detector; E is a unit matrix; A is a kernel matrix, and a matrix of a reference spectrum measured under the driving conditions of each light source; and a is a unit of noise removal. The Equation 2 may be solved using any known method, e.g., a least square method which may be solved using, e.g., QR decomposition.

Figure 3A:
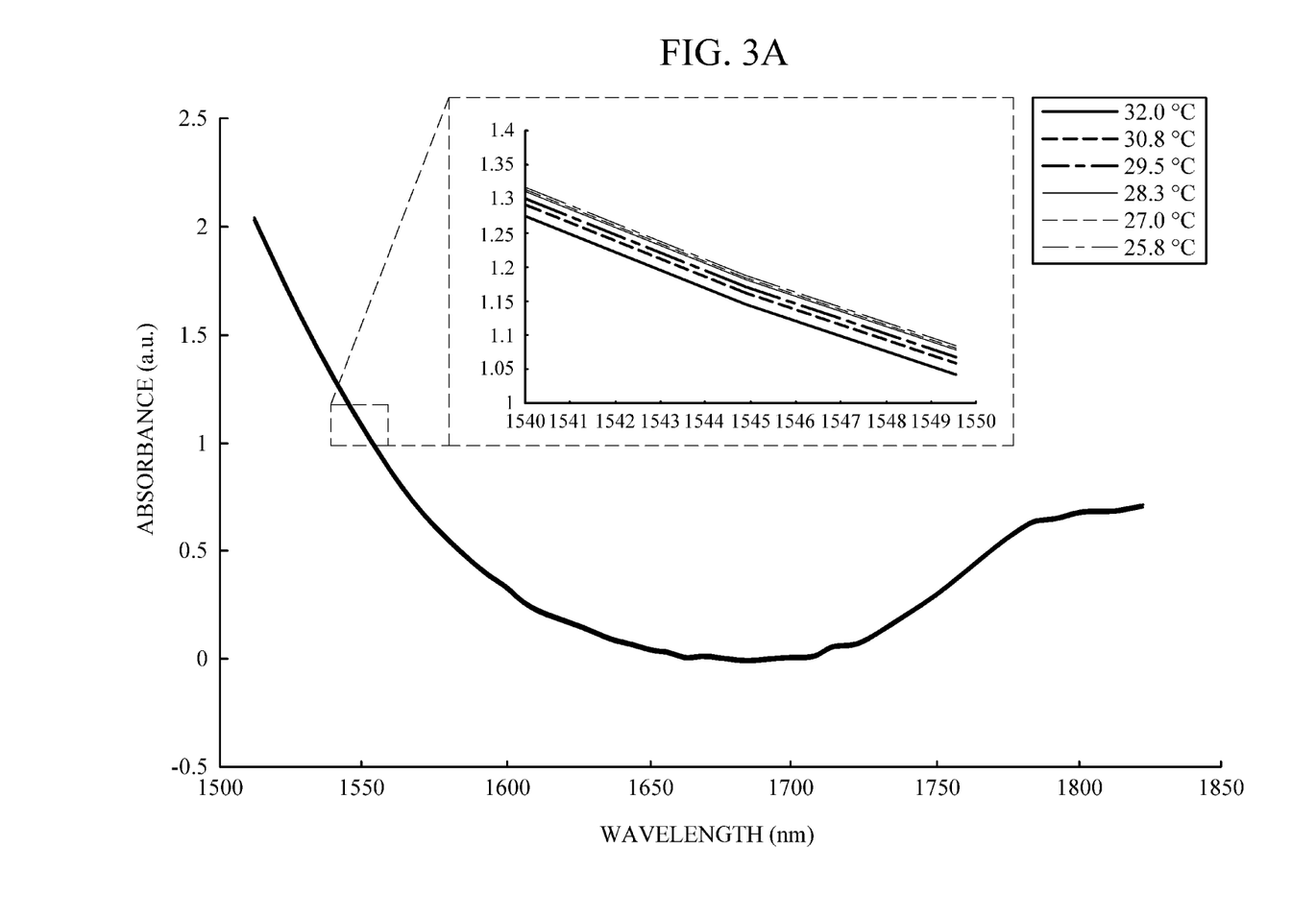
FIGS. 3A to 3C are diagrams explaining a spectrum processing process according to an example embodiment.
Figure 3B:
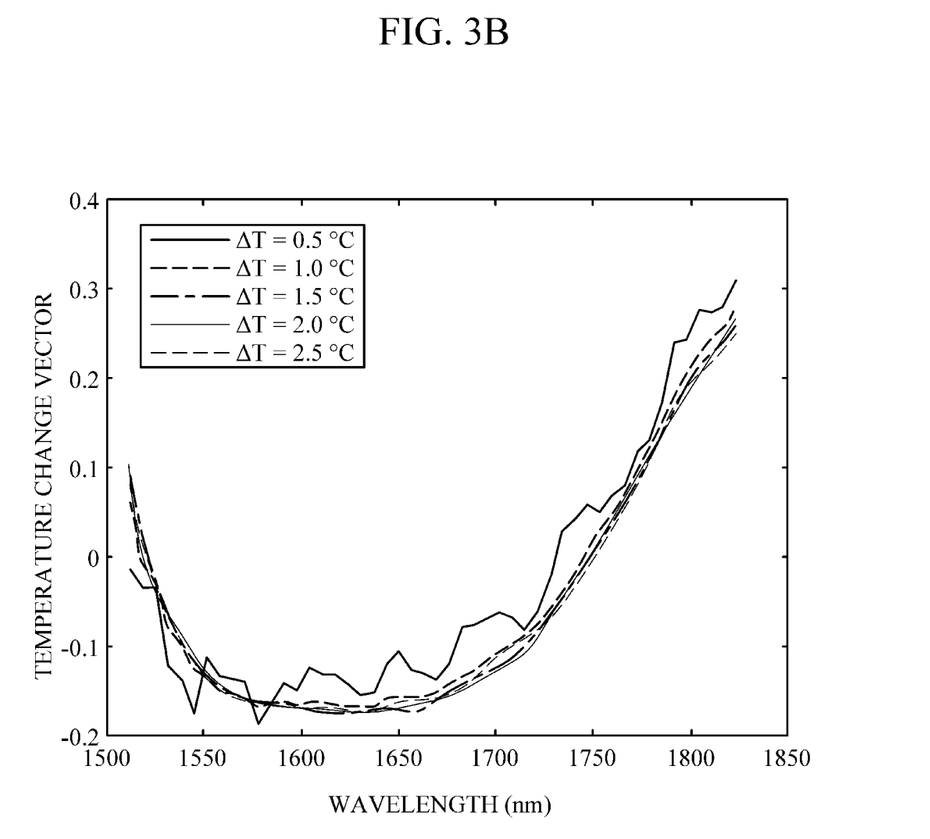
Figure 3C:
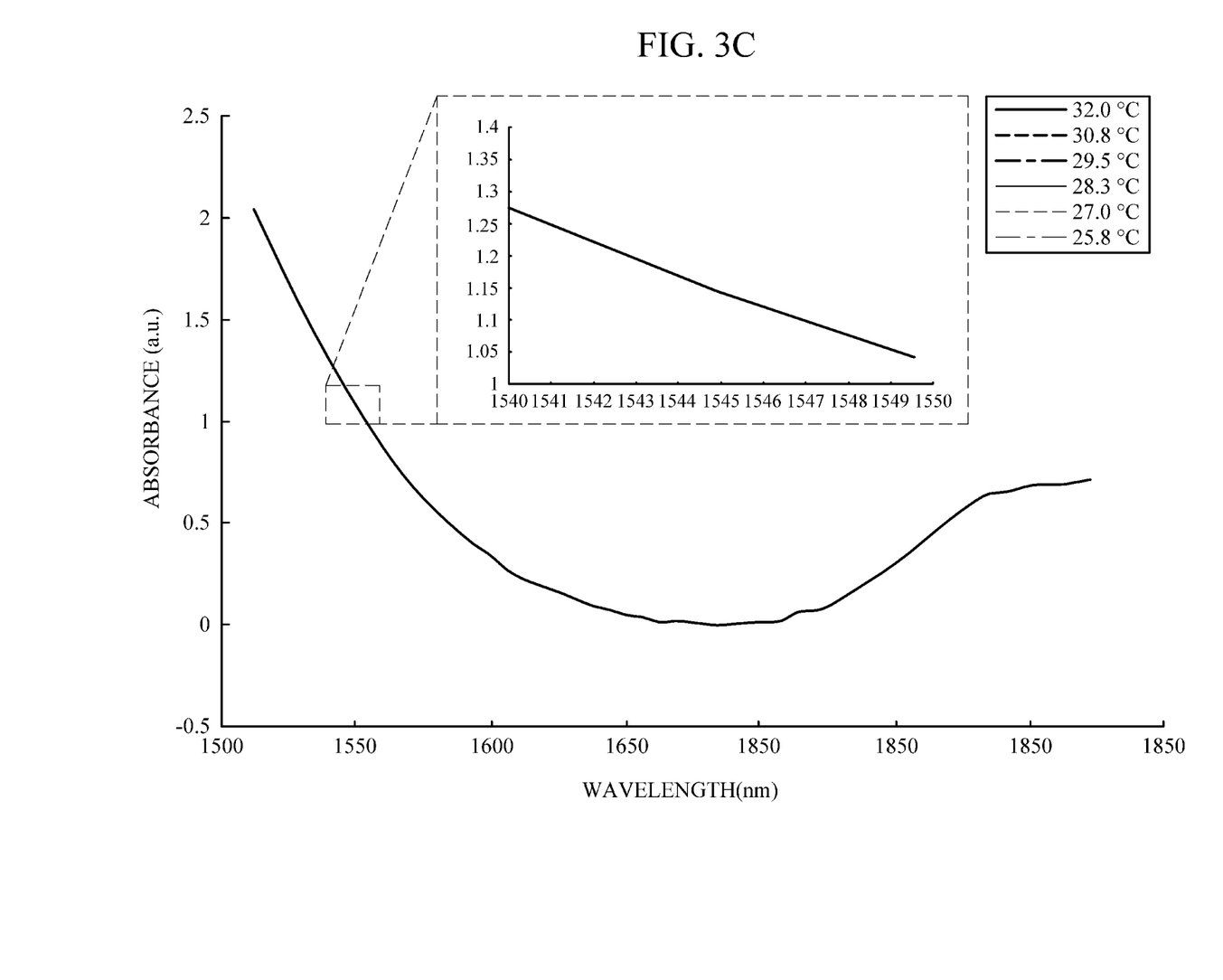

FIGS. 3A to 3C are diagrams explaining a spectrum processing process according to an example embodiment.

Referring to FIGS. 1 to 3C, an example of processing a spectrum according to a change in temperature by the spectrum processing apparatus 100 will be described below.

FIG. 3A is a diagram illustrating a change in absorbance of a spectrum according to a change in temperature of an object by modulation of temperature. As illustrated in FIG. 3A, as the temperature modulator 120 gradually modulates the temperature of the object from 25.8° C. to 32.0° C., absorbance of a spectrum obtained by the spectrometer 110 is gradually decreased. Generally, the spectrum obtained by the spectrometer 110 is affected by a change in temperature, in which in the case of near-infrared spectroscopy, when temperature is changed by 1° C., absorbance is generally changed by about $10^{-3}$. Accordingly, in an environment where temperature is not maintained at a constant level, it may be difficult to obtain a spectrum with high sensitivity by using the spectrometer 110. Thus, it is desirable to correct characteristics of respective wavelengths of the obtained spectrum according to a change in temperature.

FIG. 3B is a diagram illustrating a temperature change vector extracted from the spectrum for each temperature of FIG. 3A using Principal Component Analysis (PCA), Singular Value Decomposition (SVD), and the like. As illustrated in FIG. 3B, the extracted temperature change vector represents characteristics of respective wavelengths of the spectrum according to a change in temperature.

FIG. 3C is a diagram illustrating a correction result of the spectrum of FIG. 3A by the spectrum processor 130 using the temperature change vector of FIG. 3B. As illustrated in FIG. 3C, noise caused by a change in temperature may be removed from the measured spectrum by applying a least square method and the like.

Figure 4:
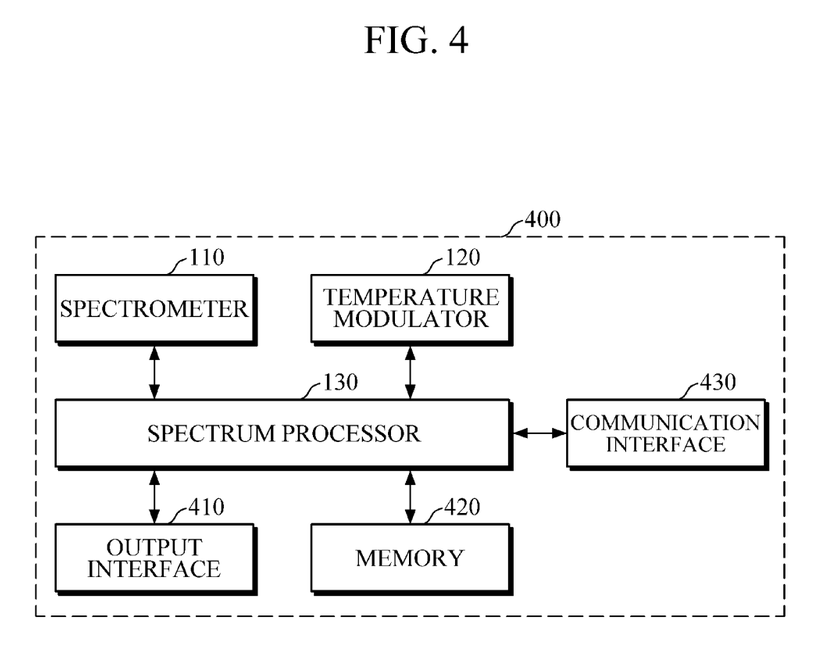
FIG. 4 is a block diagram illustrating a spectrum processing apparatus according to another embodiment.

FIG. 4 is a block diagram illustrating a spectrum processing apparatus according to another embodiment.

Referring to FIG. 4, the spectrum processing apparatus 400 includes the spectrometer 110, the temperature modulator 120, the spectrum processor 130, an output interface 410 (such as output device, or output circuitry), a memory 420, and a communication interface 430. The spectrometer 110, the temperature modulator 120, and the spectrum processor 130 may be the same or similar to those corresponding elements described above. Repetitive descriptions will be omitted and the following description will be mainly with regards to the output interface 410, the memory 420, and the communication interface 430.

The output interface 410 may output various types of information processed by the spectrum processor 130. The output interface 410 may include a visual output module such as a display and the like, an audio output module such as a speaker and the like, a haptic module generating vibrations or tactile sensation, and the like. For example, the output interface 410 may output a corrected spectrum. In this case, the output interface 410 may output a spectrum before correction and/or a temperature change vector along with the corrected spectrum.

The memory 420 may store various information such as user feature information, information on driving conditions of light sources of the spectrometer 110, and the like. Further, the memory 420 may store a processing result of the spectrum processor 130, e.g., a background spectrum, a temperature change vector, and spectra before and after noise removal.

The memory 420 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 430 may be connected to an external device through wired and wireless communications, and may receive various types of information from the external device. Examples of the external device may include an information processing device such as a smartphone, a tablet PC, a laptop computer, a desktop computer, and the like, but the external device is not limited thereto, and depending on an embodiment, may have a function of analyzing components of an object.

For example, the communication interface 430 may receive a request for measuring a spectrum for component analysis of an object from the external device, and may transmit the received request to the spectrum processor 130. In this case, the spectrum processor 130 may control the spectrometer 110 in response to the request for measuring the spectrum. Further, the communication interface 430 may receive criteria, such as the driving conditions of the light sources and the like, from the external device, and may transmit the received criteria to the spectrum processor 130. In this case, the spectrum processor 130 may store the received criteria in the memory 420. In addition, the communication interface 430 may transmit a processing result of the spectrum processor 130 to the external device.

The communication interface 430 may communicate with the external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 5:
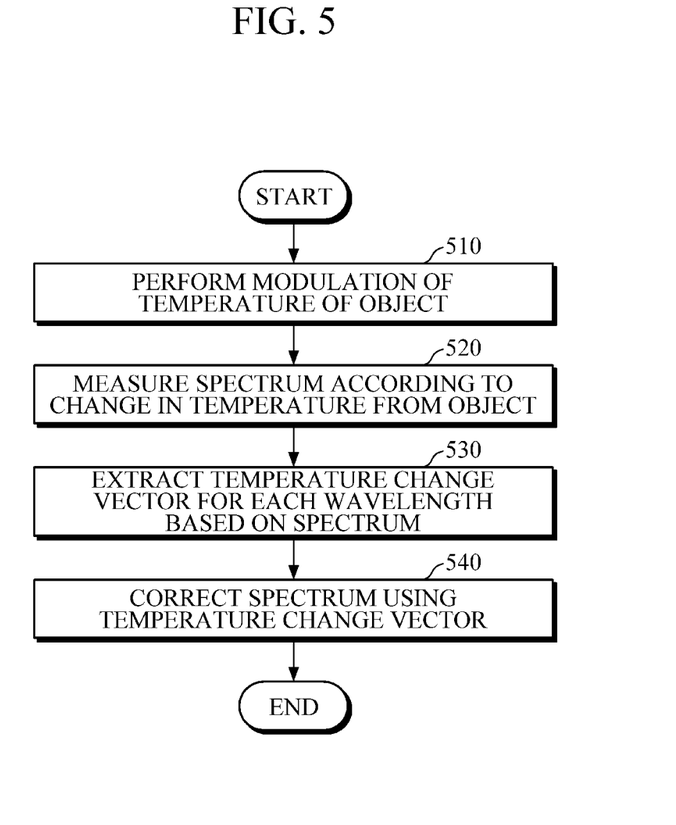
FIG. 5 is a flowchart illustrating a spectrum processing method according to an example embodiment.

FIG. 5 is a flowchart illustrating a spectrum processing method according to an example embodiment.

The embodiment of FIG. 5 may be an example of a spectrum processing method performed by any one of the spectrum processing apparatuses 100 and 400 described above.

Referring to FIG. 5, the spectrum processing apparatus may perform modulation of temperature of an object in 510. The temperature modulation of the object may be performed according to a modulation condition predetermined in consideration of various measurement circumstances. The modulation of temperature may be performed several times during a predetermined period of time, and may be performed to change temperature by 1° C. or more, so as to minimize effects derived from factors other than temperature.

Then, the spectrum processing apparatus may measure a spectrum according to a change in temperature from the object during modulation of temperature of the object in 520. In this case, the object may include a pure water solution, a human skin tissue containing a target component, and the like, but is not limited thereto.

Subsequently, the spectrum processing apparatus may extract a temperature change vector, which represents characteristics of respective wavelengths, based on a spectrum for each temperature which is changed by modulation of temperature in 530. For example, the spectrum processing apparatus may extract the temperature change vector by using Principal Component Analysis (PCA). Singular Value Decomposition (SVD), and the like. In this case, the temperature change vector may include noise of a spectrum which is caused by a temperature change.

Next, the spectrum processing apparatus may correct a spectrum by using the extracted temperature change vector in 540. For example, the spectrum processing apparatus may remove noise for each wavelength, which is caused by a temperature change, from a spectrum by using a least square method and the like based on the temperature change vector which represents characteristics of respective wavelengths according to a temperature change. In this case, the corrected spectrum may be the spectrum measured in 520, or a spectrum which is not illustrated but measured from the object, such as human skin, for analysis of a target component.

Figure 6:
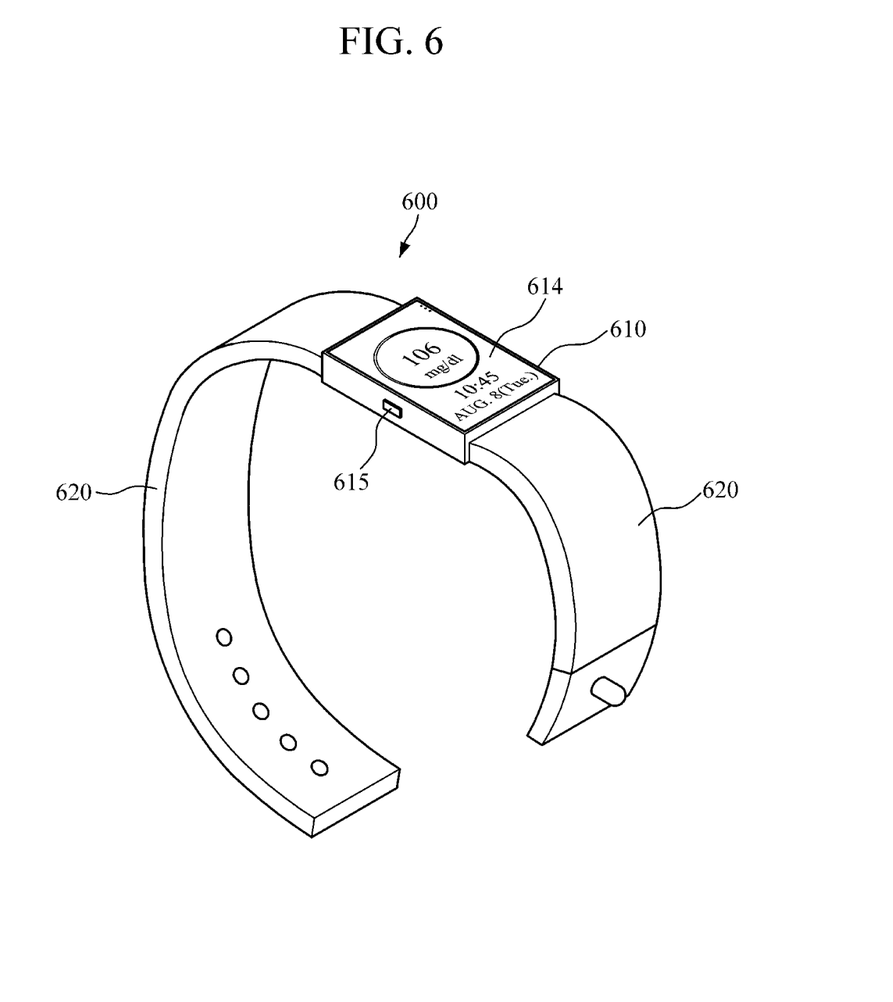
FIG. 6 is a diagram schematically illustrating a structure of a biological component analyzing apparatus according to an example embodiment.
Figure 7:
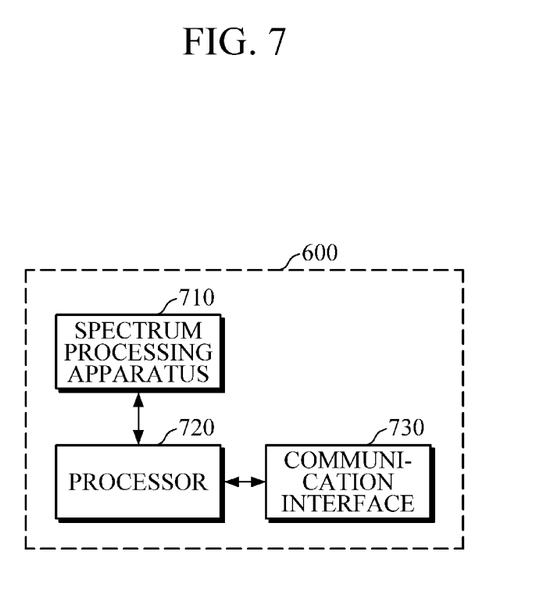
FIG. 7 is a block diagram illustrating the biological component analyzing apparatus of FIG. 6.

FIG. 6 is a diagram schematically illustrating a structure of a biological component analyzing apparatus according to an example embodiment. FIG. 7 is a block diagram illustrating the biological component analyzing apparatus of FIG. 6.

As illustrated in FIG. 6, an example of a biological component analyzing apparatus 600 may be a smart watch-type wearable device. However, the wearable device is not limited thereto, and may be modified in various forms such as a smartphone, a tablet PC, a smart band, and the like. The biological component analyzing apparatus 600 of FIGS. 6 and 7 may include the aforementioned spectrum processing technique.

Referring to FIGS. 6 and 7, the biological component analyzing apparatus 600 includes a main body 610 and a strap 620.

The strap 620 may be connected to the main body 610, and may be flexible such that the strap 620 may be bent around a user's wrist or may be bent in a manner which allows the strap 620 to be detached from the user's wrist. In this case, a battery, which supplies power to the biological component analyzing apparatus 600, may be embedded in the main body 610 or the strap 620.

Further, a spectrum processing apparatus 710 and a processor 720 may be mounted in the main body 610. The spectrum processing apparatus 710 may be disposed at a rear surface of the main body 610 to come into contact with a user's wrist (e.g., a top portion of the user's wrist). As illustrated in FIGS. 1 and 2, the spectrum processing apparatus 710 may include the spectrometer, the temperature modulator, and the spectrum processor. The spectrometer may include a light source having an array of a plurality of LEDs and a detector. The temperature modulator may include a heater and a temperature sensor. According to example embodiments, the spectrum processor may also be included in the processor 720.

Upon receiving a request for analyzing a biological component from a user, the processor 720 may control the spectrum processing apparatus 710.

The spectrum processing apparatus 710 may drive the spectrometer to obtain a spectrum from the user's wrist under the control of the processor 720. In this case, the spectrometer may emit light in a near-infrared range or a mid-infrared range. The spectrometer may include a Linear Variable Filter (LVF). The LVF has spectral properties which vary linearly over the entire length. Accordingly, the LVF may scatter the incident light in order of wavelengths. Although having a compact size, the LVF has excellent light scattering ability.

In addition, the spectrum processing apparatus 710 may modulate temperature of an object during measurement of a spectrum. The temperature modulator may modulate temperature one or more number of times according to a predetermined range of temperature, a number of times of change, and the like, and may change temperature by 1° C. or more in an operation of temperature modulation. Such condition for modulation may be optimized according to the computing performance and size of the biological component analyzing apparatus 700, a measurement portion, individual characteristics of users, and the like. In an example embodiment, the spectrum processing apparatus 710 may perform modulation of temperature of the object by driving the temperature modulator at the time of calibration and/or estimation of a biological component. That is, the modulation of temperature may be performed only at the time of calibration and may not be performed at the time of analyzing a biological component.

Once the spectrometer obtains a spectrum according to a change in temperature by modulation of temperature, the spectrum processor of the spectrum processing apparatus 710 may extract a temperature change vector, which represents characteristics of respective wavelengths according to the change in temperature, from the obtained spectrum, and may correct a spectrum for analysis of a biological component by using the extracted temperature change vector. In this case, the spectrum processor may remove noise, caused by the change in temperature, from the spectrum by using a least square method and the like.

The processor 720 may be connected to the spectrum processing apparatus 710 to control the spectrum processing apparatus 710. For example, upon receiving a request for estimating a biological component, the processor 720 may control the spectrum processing apparatus 710.

Once a spectrum, from which noise caused by the change in temperature is removed, is output, the processor 720 may analyze a biological component based on the output spectrum. For example, a biological component to be analyzed may include in vivo components such as blood glucose, calories, triglycerides, alcohol, and the like. In this case, the processor 720 may obtain an analysis result of a biological component by using a component estimation model which is pre-generated according to components to be analyzed. For example, for the analysis of blood glucose, a blood glucose estimation model may be built by using the Beer-Lambert law.

The processor 720 may determine whether to perform calibration according to a change in an estimation environment, an estimation result of a biological component and/or a user's request. For example, upon collecting location information of a user, in the case where the user moves to an area in which external temperature is changed significantly compared to a previous measurement area, the processor 720 may determine to newly perform calibration. Further, in the case where a predetermined condition for calibration is satisfied, such as a case where a total number of times an estimated biological component value is not within a normal range is greater than or equal to a predetermined threshold, or a case where abnormality greater than or equal to a predetermined threshold successively occurs within a predetermined period of time, the processor 720 may determine to perform calibration.

Upon determining that calibration is to be performed, the processor 720 may control the spectrum processing apparatus 710 to re-obtain a temperature change vector. In this case, the spectrum processing apparatus 710 may perform modulation of temperature to change temperature of an object, and may extract a temperature change vector, which represents characteristics of respective wavelengths, from the measured spectrum according to a change in temperature of the object.

The biological component analyzing apparatus 600 may further include a manipulator 615 and a display 614 which are mounted in the main body 610. The manipulator 615 receives a user command and transmits the received command to the processor 720. The manipulator 615 may include a power button to turn on/off the biological component analyzing apparatus 600.

Under the control of the processor 720, the display 614 may provide additional information, such as an analysis result of components, warning and alarm information, and the like, to a user by various visual methods.

Further, the biological component analyzing apparatus 600 may include a communication interface 730 which communicates with an external device such as a user's mobile terminal, a smartphone, a tablet PC, a desktop computer, a laptop computer, and the like. The communication interface 730 may be mounted in the main body 610.

According to the embodiments described above, accuracy may be further improved compared to a case where blood glucose values are calculated using a spectrum obtained by applying multiplicative scatter correction (MSC).

The example embodiments may be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for implementing the example embodiments can be easily deduced by one of ordinary skill in the art.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

While a few example embodiments have been described above, the scope of the disclosure is not limited thereto and various modifications and improvements made by those of ordinary skill in the art to concepts defined in the following claims should be understood to fall within the scope of the disclosure.

What is claimed is:

1. A spectrum processing apparatus comprising:
a temperature modulator configured to perform modulation of a temperature of an object;
a spectrometer configured to obtain a first spectrum based on the temperature of the object which is changed by the modulation; and
a spectrum processor configured to extract a temperature change vector, which represents characteristics of respective wavelengths according to a change in the temperature, based on the first spectrum, and to correct a second spectrum based on the extracted temperature change vector,
wherein the spectrometer comprises:
at least one light source configured to emit light onto the object; and
a detector configured to detect light scattered and/or reflected from the object, and
wherein the spectrum processor is further configured to remove noise, caused by the change in the temperature, from the second spectrum by applying a noise removal method including a least square method based on the extracted temperature change vector.

2. The spectrum processing apparatus of claim 1, wherein the temperature modulator comprises:
a heater configured to supply heat energy to the object; and
a temperature sensor configured to detect the temperature of the object.

3. The spectrum processing apparatus of claim 1, wherein the temperature modulator is further configured to perform the modulation to change the temperature of the object by 1° C. or more.

4. The spectrum processing apparatus of claim 1, wherein the temperature modulator is further configured to perform the modulation at least one time to change the temperature of the object within a predetermined range of temperature.

5. The spectrum processing apparatus of claim 4, wherein the temperature modulator is further configured to successively perform first modulation and second modulation, such that the temperature of the object is continuously increased by the first modulation and the second modulation within the predetermined range of temperature.

6. The spectrum processing apparatus of claim 4, wherein the temperature modulator is further configured to perform first modulation of the temperature, and perform second modulation in response to the temperature of the object being decreased to a temperature at a time of starting the first modulation, such that the temperature of the object is changed by the first modulation within the same range as a changed temperature of the object by the second modulation.

7. The spectrum processing apparatus of claim 1, wherein the spectrometer is further configured to obtain the first spectrum by using at least one of Infrared spectroscopy and Raman spectroscopy.

8. The spectrum processing apparatus of claim 1, wherein the spectrum processor is further configured to extract the temperature change vector based on at least one of Principal Component Analysis (PCA) and Singular Value Decomposition (SVD).

9. The spectrum processing apparatus of claim 1, wherein the spectrometer is further configured to:
obtain the first spectrum from the object that comprises at least one of a pure water solution and human skin containing a target component, and
obtain the second spectrum from a second object comprising the human skin containing the target component.

10. The spectrum processing apparatus of claim 9, further comprising an output interface configured to output a processing result of the spectrum processor.

11. The spectrum processing apparatus of claim 9, further comprising a communication interface configured to transmit a processing result of the spectrum processor to an external device.

12. A spectrum processing method comprising:
performing modulation of a temperature of an object;
obtaining, using a spectrometer, a first spectrum based on the temperature of the object which is changed by the modulation, the spectrometer comprising at least one light source configured to emit light onto the object, and a detector configured to detect light scattered and/or reflected from the object;
extracting a temperature change vector, which represents characteristics of respective wavelengths according to a change in the temperature, based on the first spectrum; and
correcting a second spectrum based on the extracted temperature change vector,
wherein the correcting the second spectrum comprises removing noise, caused by the change in the temperature, from the second spectrum by applying a noise removal method including a least square method based on the extracted temperature change vector.

13. The spectrum processing method of claim 12, wherein the performing the modulation comprises performing the modulation to change the temperature of the object by 1° C. or more.

14. The spectrum processing method of claim 12, wherein the performing the modulation comprises performing the modulation at least one time to change the temperature of the object within a predetermined range of temperature.

15. The spectrum processing method of claim 12, wherein the extracting the temperature change vector comprises extracting the temperature change vector based on at least one of Principal Component Analysis (PCA) and Singular Value Decomposition (SVD).

16. The spectrum processing method of claim 12, wherein the obtaining comprises obtaining the first spectrum from the object that comprises at least one of a pure water solution and human skin containing a target component,
the spectrum processing method further comprising:
obtaining the second spectrum from a second object that comprises the human skin containing the target component.

17. The spectrum processing method of claim 13, further comprising outputting the corrected second spectrum.

* * * * *